United States Patent [19]

Chasar

[11] Patent Number: 4,529,533
[45] Date of Patent: Jul. 16, 1985

[54] SUBSTITUTED 2-(2,6-DI-T-BUTLY-4-ALKYLPHENOXY) 4H-1,3,2-BENZODIOXAPHOSPHORINS AND COMPOSITIONS THEREOF

[75] Inventor: Dwight W. Chasar, Northfield, Ohio

[73] Assignee: The B. F. Goodrich Company, Akron, Ohio

[21] Appl. No.: 419,361

[22] Filed: Sep. 17, 1982

[51] Int. Cl.$^3$ .......................... C07F 9/28; C08K 5/53
[52] U.S. Cl. .................................. 524/101; 524/117; 524/118; 252/405; 252/400 R; 260/936; 260/967
[58] Field of Search .............................. 260/936, 967; 252/400.24, 405; 524/101, 117, 118; 106/169, 177, 270, 243

[56] References Cited

U.S. PATENT DOCUMENTS

| | | |
|---|---|---|
| 2,944,074 | 7/1960 | Atherton . |
| 3,022,330 | 2/1962 | Lanham ............................... 524/117 |
| 3,531,483 | 9/1970 | Gilles .................................... 524/101 |
| 4,025,486 | 5/1977 | Gilles . |
| 4,415,686 | 11/1983 | Chasar ............................... 252/400.2 |
| 4,439,564 | 3/1984 | Chasar ............................... 252/400.2 |

OTHER PUBLICATIONS

Biryukov et al., C.A. 76(14):73172m, Effectiveness of Mixtures of Stabilizers Possessing an Antioxidizing Synergetic Effect.

Kirpichnikov et al., CA 75 (26):152489c, Protection of Polymers by Phosphorous Acid Esters from Derivatives of Metals of Variable Valance.

Kirpichnikov et al., CA 73(4):15657a, Phosphorous Acid Esters as Colorless Stabilizers of Low-Pressure Polyethylene.

*Primary Examiner*—John Kight
*Assistant Examiner*—Garnette D. Draper
*Attorney, Agent, or Firm*—J. Hughes Powell, Jr.; Nestor W. Shust

[57] ABSTRACT

Substituted 2-(2,6-di-t-butyl-4-alkylphenoxy)-4H-1,3,2-benzodioxaphosphorins that are readily prepared, for example from hindered phenols and ortho-methylolphenols, are effective heat and anti-oxidant stabilizers for organic materials subject to degradation by heat and oxygen, and provide particularly efficient stabilizer systems when combined with hydroxyphenylalkyleneyl isocyanurates.

18 Claims, No Drawings

SUBSTITUTED 2-(2,6-DI-T-BUTLY-4-ALKYLPHENOXY) 4H-1,3,2-BENZODIOXAPHOSPHORINS AND COMPOSITIONS THEREOF

BACKGROUND OF THE INVENTION

A number of aromatic and cyclic phosphorus containing stabilizers for polymers are known. Some of these are effective against heat degradation of polymers and some of them find use in combination with other stabilizers for the same or different functions, protection against ultra-violet light degradation for example. Many of these cyclic phosphorus containing materials are expensive and they have varying degrees of effectiveness when combined with other stabilizers. Further, some of the most effective materials have some deficiencies such as lack of hydrolytic stability and the like. New cyclic phosphites that are effective anti-oxidants, are readily and inexpensively prepared, and that particularly exhibit enhanced polymer protection when combined with hydroxyphenylalkylenyl isocyanurate compounds are desired.

SUMMARY OF THE INVENTION

Substituted 2-(2,6-di-t-butyl-4-alkylphenoxy)-4H-1,3,2,-benzodioxaphosphorins that are readily prepared, for example from hindered phenols and ortho-methylolphenols, are effective heat and anti-oxidant stabilizers for organic materials subject to degradation by heat and oxygen, and provide particularly efficient stabilizer systems when combined with hydroxyphenylalkyleneyl isocyanurates.

DETAILED DESCRIPTION

The substituted 2-(2,6-di-t-butyl-4-alkylphenoxy)4H-1,3,2,-benzodioxaphosphorins have the following generic formula:

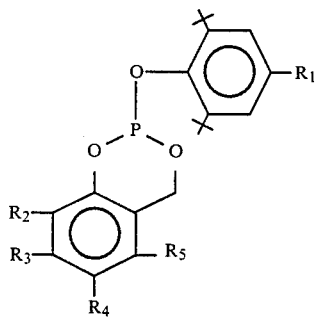

wherein:

+ is t-butyl;

$R_1$ is hydrogen, an alkyl radical containing 1 to 8 carbon atoms, a cycloalkyl radical containing 3 to 6 carbon atoms, halogen, an alkoxy radical containing 1 to 8 carbon atoms, phenyl, a —$CH_2CH_2COOR_6$ group wherein $R_6$ is an alkyl radical containing 1 to 8 carbon atoms, or a t-alkyl radical containing 4 to 8 carbon atoms, and when $R_1$ is t-butyl, no more than three of $R_2$, $R_3$, $R_4$ and $R_5$ are hydrogen, and preferably at least one of said $R_2$, $R_3$, $R_4$ or $R_5$ groups is alkyl containing 1 to 8 carbon atoms;

$R_2$ is hydrogen, an alkyl radical containing 1 to 8 carbon atoms, and methoxy or phenyl when $R_3$, $R_4$ and $R_5$ are hydrogen, or when $R_3$ and $R_4$ are hydrogen and $R_5$ is methyl;

$R_3$ is methyl when $R_4$ is methyl or hydrogen and $R_2$ and $R_5$ are hydrogen;

$R_4$ is hydrogen, an alkyl radical containing 1 to 8 carbon atoms, a cycloalkyl radical containing 3 to 6 carbon atoms, a t-alkyl radical containing 4 to 8 carbon atoms, methoxy, phenyl, halogen or methoxycarbonyl, when $R_2$ is hydrogen, an alkyl radical containing 1 to 8 carbon atoms, a cycloalkyl radical containing 3 to 6 carbon atoms and a t-alkyl radical containing 4 to 8 carbon atoms, and $R_3$ and $R_5$ are hydrogen;

$R_5$ is methyl when $R_2$, $R_3$ and $R_4$ are hydrogen, or when $R_4$ is methyl and $R_2$ and $R_3$ are hydrogen, and hydrogen when $R_2$, $R_3$, $R_4$ are the same as above;

and when $R_4$ and $R_5$ are (—CH=$CR_7$—CH=CH—), $R_7$ is hydrogen or t-butyl, and $R_2$ is t-butyl or hydrogen and $R_3$ is hydrogen; and when $R_2$ and $R_3$ are (—CH=CH—)$_2$, $R_4$ and $R_5$ are hydrogen.

A preferred group of compounds is obtained when $R_1$ is hydrogen, a primary, secondary or tertiary alkyl group containing 1 to 4 carbon atoms as defined, or a —$CH_2CH_2COOR_6$ group wherein $R_6$ is an alkyl radical containing 1 to 4 carbon atoms; $R_2$ is hydrogen, a primary, secondary or tertiary alkyl radical containing 1 to 4 carbon atoms; $R_3$ is hydrogen or methyl; $R_4$ is hydrogen or a primary, secondary or tertiary alkyl radical containing 1 to 4 carbon atoms; and $R_5$ is hydrogen.

An even more preferred group of compounds is obtained when $R_1$ is —H, —$CH_3$, —t—$C_4H_9$ as defined or —$CH_2CH_2COOCH_2CH_3$; $R_2$ is —H, —$CH_3$, or —t—$C_4H_9$; $R_3$ is —H; $R_4$ is —H, —$CH_3$, or —t—$C_4H_9$; and $R_5$ is H.

Typical compounds include 2-[4-methyl-2,6-bis(1,1-dimethylethyl)phenoxy]-6,8-bis(1,1-dimethylethyl)-4H-1,3,2-benzodioxaphosphorin; 2-[4-methyl-2,6-bis(1,1-dimethylethyl)phenoxy]-4H-1,3,2-benzodioxaphosphorin; 2-[4-methyl-2,6-bis(1,1-dimethylethyl)phenoxy]-6-methyl-4H-1,3,2-benzodioxaphosphorin; 2-[4-methyl-2,6-bis(1,1-dimethylethyl)phenoxy]-6,8-dimethyl-4H-1,3,2-benzodioxaphosphorin; 2-[4-methyl-2,6-bis(1,1-dimethylethyl)phenoxy]-8-(1,1-dimethylethyl)-4H-1,3,2-benzodioxaphosphorin; 2-[4-methyl-2,6-bis(1,1-dimethylethyl)phenoxy]-6-(1,1-dimethylethyl)-8-methyl-4H-1,3,2-benzodioxaphosphorin; 2-[4-methyl-2,6-bis(1,1-dimethylethyl)phenoxy]-6-methyl-8-(1,1-dimethylethyl)-4H-1,3,2-benzodioxaphosphorin; 2-[2,4,6-tris(1,1-dimethylethyl)phenoxy]-6,8-bis(1,1-dimethylethyl)-4H-1,3,2-benzodioxaphosphorin; 2-[2,4,6-tris(1,1-dimethylethyl)phenoxy]-6-methyl-4H-1,3,2-benzodioxaphosphorin; 2-[2,4,6-tris(1,1-dimethylethyl)phenoxy]-6,8-di-methyl-4H-1,3,2-benzodioxaphosphorin; 2-[2,4,6-tris(1,1-dimethylethyl)phenoxy]-8-(1,1-dimethylethyl)-4H-1,3,2-benzodioxaphosphorin; 2-[2,4,6-tris(1,1-dimethylethyl)phenoxy]-6-(1,1-dimethylethyl)-8-methyl-4H-1,3,2-benzodioxaphosphorin; 2-[2,6-bis(1,1-dimethylethyl)-4-(2-ethoxycarbonylethyl)phenoxy]-6,8-bis(1,1-dimethylethyl)-4H-1,3,2-benzodioxaphosphorin; 2-[2,6-bis(1,1-dimethylethyl)-4-(2-ethoxycarbonylethyl)phenoxy]-6,8-dimethyl-4H-1,3,2-benzodioxaphosphorin; and the like.

The cyclic phosphites of this invention are the reaction products of hindered phenols, ortho-methylolphenols and phosphorous trichloride, to form a family of substituted 2-(2,6-di-t-butyl-4-alkylphenoxy)-4H-1,3,2-benzodioxaphosphorins.

The ortho-methylolphenols have the general formula

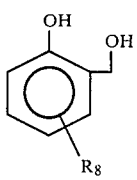

wherein $R_8$ is 1 to 4 hydrogen or alkyl groups containing 1 to 12, preferably 1 to 8 carbon atoms. The preparation of these materials is reported in the literature, and may be made for example by reacting phenols such as p-cresol and 2,4-dimethylphenol with aqueous formaldehyde in caustic solution. Another procedure is to conduct the reaction of the phenol and para formaldehyde with boric acid in solution. Typical ortho-methylolphenols are 2,4-dimethyl-6-hydroxymethylphenol, 2,4-di-t-butyl-6-hydroxymethylphenol, and the like.

The hindered phenols have the general formula

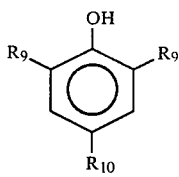

wherein $R_9$ is t-alkyl groups containing from 4 to 12 carbon atoms, but preferably are t-butyl, and $R_{10}$ is hydrogen, t-alkyl as defined, or alkyl radical containing 1 to 8 carbon atoms, or an ester group, $COOR_{11}$ wherein $R_{11}$ is an alkyl group containing 1 to 8 carbon atoms and a $CH_2CH_2COOR_6$ group wherein $R_6$ contains 1 to 8 carbon atoms; such as 2,4,6-tri-t-butylphenol, 2,6-di-t-butyl-4-methylphenol, and the like.

The cyclic phosphites are prepared by reacting the ortho-methylolphenol with the hindered phenol using phosphorous trichloride and a trialkylamine as a catalyst. A preferred method for preparing the cyclic phosphites is to react the ortho-methylolphenol, a phosphorodichloridite, in an organic solvent in the presence of the trialkylamine catalyst. The cyclic phosphite is isolated from the reaction mixture and purified with solvents, preferably at temperatures below 100° C., more preferably below about 75° C. Typical preparations of the ortho-methylolphenols and cyclic phosphites therefrom are set forth in the following examples.

2,4-Dimethyl-6-hydroxymethylphenol

A 38% solution of formaldehyde (32.0 grams, 0.4 mol) was added to a stirred solution of 2,4-dimethylphenol (36.6 grams, 0.3 mol) in water (100 ml) containing sodium hydroxide (14 gr., 0.35 mol) and heated at 50° C. for 4 to 5 hours. The reaction was cooled and solid sodium hydroxide added to precipitate the salt of the product. The solid was removed by filtration and dissolved in water. This solution was neutralized with carbon dioxide (dry ice) and the resulting mixture was extracted with methylene chloride. The organic layer was removed, dried, and evaporated to yield a light brown solid. This solid was washed in hexane containing a small amount of toluene to afford a tan solid. The NMR[1] and FD/MS[2] data support the structure.

[1]Nuclear Magnetic Resonance
[2]Field Desorption/Mass Spectrometer

2,4-Di-t-butyl-6-hydroxymethylphenol 2,4-Di-t-butylphenol (20.63 gr., 0.1 mole), paraformaldehyde (3.0 gr., 0.1 mol), boric acid (6.18 g., 0.1 mol) and toluene (50 ml.) were charged into a flask and heated at 80° C. under nitrogen for 48 hours. The mixture was filtered and the solvent removed to provide a brown oil. This oil was dissolved in ether and stirred with an equal volume of 1N HCl for 2 hours. The ether layer was removed, washed with water, dried (MgSO4) and evaporated to form a soft yellow solid. This solid was stirred in pentane and then filtered to afford a white solid with a melting point of 97°–99° C. The structure was confirmed by NMR and FD/MS.

2-(2,4,6-tri-t-butylphenoxy)-6,8-dimethyl-4H-1,3,2-benzodioxaphosphorin 2,4-dimethyl-6-hydroxymethylphenol (7 g., 0.046 mol) was dissolved in dry THF (75 ml.) and cooled to 0° C. Under nitrogen, 2,4,6-tri-t-butylphenylphosphorodichloridite (16.85 g., 0.046 mol) was added to the solution. Triethylamine (9.4 g., 0.093 mol) was added dropwise to the cooled stirred solution. After 3.5 hours, the reaction mixture was filtered and the filtrate was evaporated to dryness to form an off-white friable glass. The glass was stirred in acetonitrile for 2 hours to obtain a white solid, melting point of 133°–138° C. The HNMR and FD/MS support this structure.

Using the same procedure set forth above, 2-[4-methyl-2,6-bis(1,1-dimethylethyl)phenoxy]-4H-1,3,2-benzodioxaphosphorin was prepared from 2,6-di-t-butyl-4-methylphenylphosphorodichloridite and salicyl alcohol. The crude reaction product was washed with acetonitrile. A white solid was obtained with a melting point of 80°–82° C. The structure was confirmed by NMR and Infra-Red. Also 2-[2,4,6-tri(1,1-dimethylethyl)phenoxy]-6-methyl-4H-1,3,2-benzodioxaphosphorin was prepared from 2,4,6-tri-t-butylphenylphosphorodichlorodite and 4,-methyl-2-hydroxymethylphenol, and after washing with acetonitrile, resulted in a white powder having a melting point of 98°–100° C. The NMR and IR confirmed the structure.

2-(2,6-di-t-butyl-4-methylphenoxy)-6,8-dimethyl-4H-1,3,2-benzodioxaphosphorin This compound was made in the same manner as that above using 2,4-dimethyl-6-hydroxymethylphenol and 2,6-di-t-butyl-4-methylphenylphosphorodichloridite to obtain a white solid, melting point of 132°–138° C. The FD/MS and HNMR confirm this structure.

Other cyclic phosphites prepared as described above were 2-[4-methyl-2,6-bis(1,1-dimethylethyl)phenoxy]-6-methyl-4H-1,3,2-benzodioxaphosphorin, melting point 117°–123° C., molecular weight 486, by the reaction of 4-methyl-6-hydroxymethylphenol with 2,6-di-t-butyl-4-methylphenylphosphorodichloridite; 2-[2,4,6-tris(1,1-dimethylethyl)phenoxy]-6,8-bis(1,1-dimethylethyl)-4H-1,3,2-benzophosphorin, melting point 166°–255° C., molecular weight 526, by the reaction of 2,4,6-di-t-butyl-6-hydroxymethylphenol with 2,4,6-tri-t-butylphenylphosphorodichloridite; and 2-[2,4,6-tris(1,1-dimethylethyl)phenoxy]-8-(1,1-dimethylethyl)-4H-1,3,2-benzodioxaphosphorin, melting point 120°–127° C., molecular weight 470, by the reaction of 2-t-butyl-6-hydroxymethylphenol and 2,4,6-tri-t-butyl-phenylphosophorodichloridite. The structures were confirmed by Nuclear Magnetic Resonance and Infra-Red Analysis.

The hydroxyphenylalkyleneyl isocyanurate compounds used in combination with the cyclic phosphites of this invention have the formula

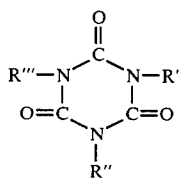

wherein R' is a hydroxyphenylalkyleneyl radical of the formula

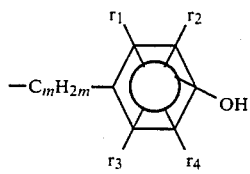

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R" and R'" are hydrogen, an alkyl radical containing 1 to 18 carbon atoms, or are the same as r'. A more preferred compound is when R" and R'" are qual to R', i.e., all the R groups are hydroxyphenylalkyleneyl radicals, and $r_1$ is a t-alkyl radical containing from 4 to about 12 carbon atoms, $r_2$ is a t-alkyl radical containing from 1 to about 12 carbon atoms, $r_3$ and $r_4$ are hydrogen, and m=1.

Even more preferred are the symmetrical tris(3,5-dit-ert-alkyl-4-hydroxybenzyl)isocyanurates of the formula

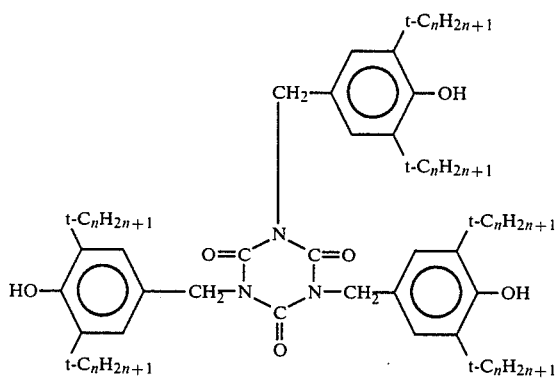

where n is 4 to 8.

Examples of the 4-hydroxybenzyl isocyanurate compounds are: tris-3-t-butyl-4-hydroxybenzyl)isocyanurate, tris-(3-cetyl-4-hydroxybenzyl)isocyanurate, tris(3,5-dimethyl-4-hydroxybenzyl)isocyanurate, tris-(3-methyl-5-isopropyl-4-hydroxybenzyl)isocyanurate, tris(3,5-di-t-butyl-4-hydroxybenzyl)isocyanurate, tris-(3-t-butyl-5-t-amyl-4-hydroxybenzyl)isocyanurate, tris-[3,5-di-(1-methyl-1-ethylpropyl)4-hydroxybenzyl-]isocyanurate, tris-[3,5,-di-(1,1,2,2-tetramethylpropyl)-4-hydroxybenzyl]]isocyanurate, bis-(3,5-dimethyl-4-hydroxybenzyl)isocyanurate, (3-methyl-4-hydroxybenzyl)isocyanurate, (3-t-butyl-4-hydroxybenzyl)isocyanurate, and the like. Reference is made to U.S. Pat. No. 3,531,483 which discloses isocyanurate compounds encompassed by this invention. The disclosure of this patent is incorporated herein by reference.

The amount of cyclic phosphite used may vary from about 0.01 to 10 weight parts per 100 weight parts of material to be stabilized. More usually about 0.1 to 4.0 parts are used for mixtures with the hydroxyphenylalkyleneyl isocyanurate. The hydroxyphenylalkyleneyl isocyanurate compound is used at a level from about 0.01 part to about 5 parts by weight, and more preferably at from about 0.05 part to about 3 parts by weight per 100 parts by weight of the organic material. The cyclic phosphite compound is employed at similar levels, i.e., from about 0.01 part to 5 parts and preferably at about 0.05 part to about 3 parts by weight per 100 parts by weight of organic material. Thus the combined weight of the compounds is normally from about 0.02 part to about 10 parts and more preferably from about 0.1 to 6 parts by weight per 100 parts by weight of organic material. The hydroxyphenylalkyleneyl isocyanurate can be used in from about 10:1 to 1:10 weight ratio of isocyanurate compound to cyclic phosphite compound. Excellent results are obtained at about a 3:1 to 1:3 weight ratio. A 1:1 weight ratio of the compounds provides effective stabilization of organic materials.

Both the cyclic phosphite and the combinations with the isocyanurate compound and the cyclic phosphite compound as defined herein provide exceptional heat stability to polyolefin polymers. The combination is especially useful for the stabilization of α-monoolefin homopolymers and copolymers, wherein the α-monoolefin contains 2 to about 8 carbon atoms. High and low-density polyethylene, isotactic and atactic polypropylene, polyisobutylene, and poly(4-methyl-1-pentene) have excellent resistance to ultra violet light when stabilized with the combinations of the present invention. Ethylene-propylene (EP) copolymers and ethylene-propylene (EPDM) terpolymers generally containing less than about 10 percent by weight of one or more monomers containing multiple unsaturation provided, for example, by 1,4-hexadiene, dimethyl-1,4,9-decatriene, dicyclopentadiene, vinyl norbornene, ethylidene norbornene and the like also are stabilized using the combination.

Other organic materials which can be stabilized in accordance with the present invention include both natural and synthetic polymers. For example, the stabilizers are useful for the stabilization of cellulosic materials; natural rubber, halogenated rubber, conjugated diene polymers, as, for instance, polybutadiene, copolymers of butadiene with styrene, acrylonitrile, acrylic acid alkyl acrylates or methacrylates, methyl vinyl ketone, vinyl pyridine, etc.; polyisoprene, polychloroprene, and the like; vinyl polymers such as polyvinyl chloride, polyvinylidene chloride, copolymers of vinyl chloride with vinylidene chloride, polyvinyl acetate, copolymers or vinyl halide with butadiene, styrene, vinyl esters, α,β-unsaturated ketones and aldehydes, and the like; homopolymers and copolymers of acrylic monomers such as methyl acrylate, methyl methacrylate, ethyl acrylate, 3-ethylhexyl acrylate, acrylamide, methacrylamide, N-methylol-acrylamide, acrylonitrile, methacrylonitrile, and the like; epihalohydrin polymers; polyether- or polyol-derived polyurethanes; acetal homo-polymers and copolymers; polycarbonates; polyesters such as those derived from maleic, fumaric, itaconic, or terephthalic anhydrides, or the like; for example, polyethylene terephthalate; polyamides such as those derived from the reaction of hexa-methylenediamine with adipic or sebacic acid; epoxy resins such as those obtained from the condensation of epichlorohydrin with bisphenols; ring opened olefin polymers and the like. Polymer blends, that is, physical admixture of two or more polymers may also be stabilized in accordance with the present invention.

In addition to polymeric materials, the present compounds may stabilize a wide variety of other organic materials. Such compounds include: waxes, synthetic and petroleum-derived lubricating oils and greases; animal oils such as, for example, fat, tallow, lard, cod-liver oil, sperm oil; vegetable oils such as castor, linseed, peanut, palm, cotton seed, and the like; fuel oil; diesel oil, gasoline, and the like.

The compounds are readily incorporated into materials by dissolving or dispersing them with the materials or in liquid, dispersion solutions and solid forms. If the material is a solid, especially a polymeric solid such as a rubber or a plastic, the compounds can be admixed using internal mixers as Banburys, extruders, two-roll mills, and the like, following conventional techniques. One way to disperse the compounds in plastic materials is to dissolve or suspend the compounds in a solvent, mix the mixture with a plastic in powder or solution form, and then evaporate the solvent.

Compositions containing the novel combination of compounds can also contain other known compounding ingredients such as fillers like carbon black, silica, metal carbonates, talc, asbestos, and the like; pigments and colorants; curative ingredients like sulfur and peroxides and vulcanization accelerators; fungicides; processing aids, reinforcing agents and standard ingredients known to the art. Other ingredients known in the art as ultra-violet light, thermal and/or oxidative stabilizers can also be used in the stabilized compositions.

Test samples were prepared by mixing the stabilizer compounds with polypropylene in a Brabender Plasticorder fitted with a Cam-Head (mixing chamber). The polypropylene is first masticated for 1½ minutes at 190° C. Then the stabilizer mixture is added, following by 3 minutes additional mixing. The mass is removed and pressed into 20 mil thick sheets. From these sheets are cut 1"×1" plaques for oven-aging. Type C (3"×⅛") tensil bars are cut for UV stability tests.

Thermal/oxidative stability (oven-aging) testing consisted of aging the samples in triplicate in an air-circulating oven at 125° C. The time to catastrophic crumbling (failure) of the plaque is measured and reported as days to failure.

Each sample contained 0.1 weight part of cyclic phosphite per 100 weight parts of polypropylene. The following results were obtained:

2-[4-methyl-2,6-bis(1,1-dimethylethyl)phenoxy]-6-methyl-4H-1,3,2-benzodioxaphosphorin, 9⅔ days;

2-[4-methyl-2,6bis(1,1-dimethylethyl)phenoxy]-6,8-dimethyl-4H-1,3,2-benzodioxaphosphorin, 7⅔ days;

2-[2,4,6-tris(1,1-dimethylethyl)phenoxy]-6,8-bis(1,1-dimethylethyl)-4H-1,3,2-benzodioxaphosphorin, 4 days;  2-[2,4,6-tris(1,1-dimethylethyl)phenoxy]-6,8-dimethyl-4H-1,3,2-benzodioxaphosphorin, 15 days; and 2-[2,4,6-tris(1,1-dimethylethyl)phenoxy]-8-(1,1-dimethylethyl)-4H-1,3,2-benzodioxaphosphorin, 5 days.

To demonstrate the unexpected synergistic enhancement of anti-oxidant activity when the cyclic phosphites of this invention are combined with a hydroxyphenylalkyleneyl isocyanurate, test samples of polypropylene with 0.05 weight part each of tris(3,5-di-t-butyl-4-hydroxy-benzyl)isocyanurate and the cyclic phosphites listed below were prepared and tested in the air oven until failure. The results obtained were as follows:

2-[4-methyl-2,6-bis(1,1-dimethylethyl)phenoxy]-6-methyl-4H-1,3,2-benzodioxaphosphorin, 39⅔ days; 2-[4-methyl-2,6-bis(1,1-dimethylethyl)phenoxy]-6,8-dimethyl-4H-1,3,2-benzodioxaphosphorin, 29⅔ days; and 2-[2,4,6-tris(1,1-dimethylethyl)phenoxy]-6,8-dimethyl-4H-1,3,2-benzodioxaphosphorin, 49 days.

These values are better than those obtained with many commercially available stabilizers in the same compositions. For example, when these tests are repeated with tris(2,4-di-t-butylphenyl)phosphite, a value of only 17⅔ days was observed; and when repeated with the phosphite alone, without the isocyanurate, a value of only 4⅔ days was observed.

I claim:

1. 2-(2,6-di-t-butyl-4-alkylphenoxy)-4H-1,3,2-benzodioxaphosphorin cyclic phosphites of the formula

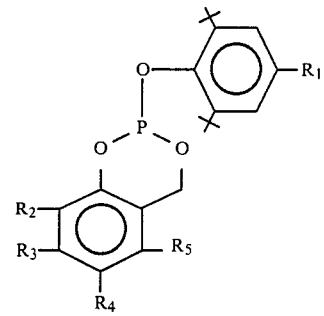

wherein:

+ is t-butyl; $R_1$ is hydrogen, an alkyl radical containing 1 to 8 carbon atoms, a cycloalkyl radical containing 3 to 6 carbon atoms, halogen, an alkoxy radical containing 1 to 8 carbon atoms, phenyl, a —$CH_2CH_2COOR_6$ group wherein $R_6$ is an alkyl radical containing 1 to 8 carbon atoms, or t-alkyl radical containing 4 to 8 carbon atoms, and when $R_1$ is t-butyl, no more than three of $R_2$, $R_3$, $R_4$ and $R_5$ are hydrogen; $R_2$ is hydrogen, an alkyl radical containing 1 to 8 carbon atoms, and methoxy or phenyl when $R_3$, $R_4$ and $R_5$ are hydrogen, or when $R_3$ and $R_4$ are hydrogen and $R_5$ is methyl; $R_3$ is methyl when $R_4$ is methyl or hydrogen and $R_2$ and $R_5$ are hydrogen; $R_4$ is hydrogen, an alkyl radical containing 1 to 8 carbon atoms, a cycloalkyl radical containing 3 to 6 carbon atoms, a t-alkyl radical containing 4 to 8 carbon atoms, methoxy, phenyl, halogen or methoxycarbonyl, when $R_2$ is hydrogen, an alkyl radical containing 1 to 8 carbon atoms, a cycloalkyl radical containing 3 to 6 carbon atoms and a t-alkyl radical containing 4 to 8 carbon atoms, and $R_3$ and $R_5$ are hydrogen; $R_5$ is methyl when $R_2$, $R_3$ and $R_4$ are hydrogen, or when $R_4$ is methyl and $R_2$ and $R_3$ are hydrogen, and hydrogen when $R_2$, $R_3$, $R_4$ are the same as above; and when $R_4$ and $R_5$ are (—CH=$CR_7$—CH=CH—), $R_7$ is hydrogen or t-butyl, and $R_2$ is t-butyl or hydrogen and $R_3$ is hydrogen; and when $R_2$ and $R_3$ are (—CH=CH—)$_2$, $R_4$ and $R_5$ are hydrogen; and at least one of said $R_2$, $R_3$ and $R_4$ is an alkyl radical containing 1 to 8 carbon atoms.

2. Cyclic phosphites of claim 1 wherein $R_1$ is hydrogen, a primary, secondary or tertiary alkyl group containing 1 to 4 carbon atoms, or a —$CH_2CH_2COOR_6$ group wherein $R_6$ is an alkyl radical containing 1 to 4 carbon atoms; $R_2$ is hydrogen, a primary, secondary tertiary alkyl radical containing 1 to 4 carbon atoms; $R_3$ is hydrogen or methyl; $R_4$ is hydrogen or a primary, secondary or tertiary alkyl radical containing 1 to 4 carbon atoms; and $R_5$ is hydrogen.

3. A cyclic phosphite of claim 2, 2-[4-methyl-2,6-bis(1,1-dimethylethyl)phenoxy]-6-methyl-4H-1,3,2-benzodioxaphosphorin.

4. A cyclic phosphite of claim 2, 2-[4-methyl-2,6-bis(1,1-dimethylethyl)phenoxy]-6,8-dimethyl-4H-1,3,2-benzodioxaphosphorin.

5. A cyclic phosphite of claim 2, 2-[2,4,6-tris(1,1-dimethylethyl)phenoxy]6,8-dimethyl-4H-1,3,2-benzodioxaphosphorin.

6. A composition comprising polyolefin materials subject to degradation and stabilizing amounts of 2-(2,6-di-t-butyl-4-alkylphenoxy)-4H-1,3,2-benzodioxaphosphorins of the formula

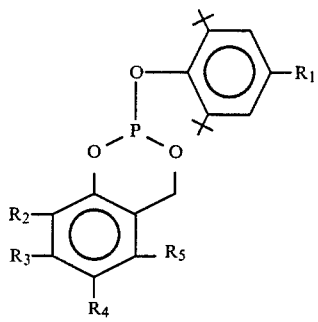

wherein:

+ is t-butyl; $R_1$ is hydrogen, an alkyl radical containing 1 to 8 carbon atoms, a cycloalkyl radical containing 3 to 6 carbon atoms, halogen, an alkoxy radical containing 1 to 8 carbon atoms, phenyl, a —$CH_2CH_2COOR_6$ group wherein $R_6$ is an alkyl radical containing 1 to 8 carbon atoms, or t-alkyl radical containing 4 to 8 carbon atoms, and when $R_1$ is t-butyl, no more than three of $R_2$, $R_3$, $R_4$ and $R_5$ are hydrogen; $R_2$ is hydrogen, an alkyl radical containing 1 to 8 carbon atoms, and methoxy or phenyl when $R_3$, $R_4$ and $R_5$ are hydrogen, or when $R_3$ and $R_4$ is hydrogen and $R_5$ is methyl; $R_3$ is methyl when $R_4$ is methyl or hydrogen and $R_2$ and $R_5$ are hydrogen; $R_4$ is hydrogen, an alkyl radical containing 1 to 8 carbon atoms, a cycloalkyl radical containing 3 to 6 carbon atoms, a t-alkyl radical containing 4 to 8 carbon atoms, methoxy, phenyl, halogen or methoxycarbonyl, when $R_2$ is hydrogen, an alkyl radical containing 1 to 8 carbon atoms, a cycloalkyl radical containing 3 to 6 carbon atoms and a t-alkyl radical containing 4 to 8 carbon atoms, and $R_3$ and $R_5$ are hydrogen; $R_5$ is methyl when $R_2$, $R_3$ and $R_4$ are hydrogen, or when $R_4$ is methyl and $R_2$ and $R_3$ are hydrogen, and hydrogen when $R_2$, $R_3$, $R_4$ are the same as above; and when $R_4$ and $R_5$ are (—CH=$CR_7$—CH=CH—), $R_7$ is hydrogen or t-butyl, and $R_2$ is t-butyl or hydrogen and $R_3$ is hydrogen; and when $R_2$ and $R_3$ are (—CH=CH—)$_2$, $R_4$ and $R_5$ are hydrogen; and at least one of said $R_2$, $R_3$, $R_4$ and $R_5$ is an alkyl radical containing 1 to 8 carbon atoms.

7. A composition of claim 6 wherein $R_1$ is hydrogen, a primary, secondary or tertiary alkyl group containing 1 to 4 carbon atoms, or a —$CH_2CH_2COOR_6$ group wherein $R_6$ is an alkyl radical contianing 1 to 4 carbon atoms; $R_2$ is hydrogen, a primary, secondary or tertiary alkyl radical containing 1 to 4 carbon atoms; $R_3$ is hydrogen or methyl; $R_4$ is hydrogen or a primary, secondary or tertiary alkyl radical containing 1 to 4 carbon atoms; and $R_5$ is hydrogen.

8. A composition of claim 7 containing polypropylene and 2-[4-methyl-2,6-bis(1,1-dimethylethyl)phenoxy]-6-methyl-4H-1,3,2-benzodioxaphosphorin.

9. A composition of claim 7 containing polypropylene and 2-[4-methyl-2,6-bis(1,1-dimethylethyl)phenoxy]-6,8-dimethyl-4H-1,3,2-benzodioxaphosphorin.

10. A composition of claim 7 containing polypropylene and 2-[2,4,6-tris(1,1-dimethylethyl)phenoxy]-6,8-dimethyl-4H-1,3,2-benzodioxaphosphorin.

11. A composition comprising polyolefin materials subject to degradation and stabilizing amounts of (1) 2-(2,6-di-t-butyl-4-alkylphenoxy)-4H-1,3,2-benzodioxaphosphorins of the formula:

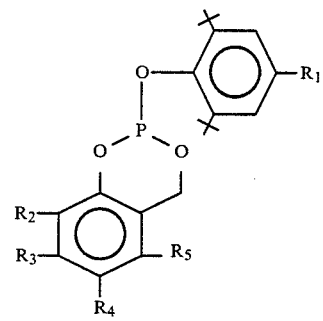

wherein:

+ is t-butyl; $R_1$ is hydrogen, an alkyl radical containing 1 to 8 carbon atoms, a cycloalkyl radical containing 3 to 6 carbon atoms, halogen, an alkoxy radical containing 1 to 8 carbon atoms, phenyl, a —$CH_2CH_2COOR_6$ group wherein $R_6$ is an alkyl radical containing 1 to 8 carbon atoms, or t-alkyl radical containing 4 to 8 carbon atoms, and when $R_1$ is t-butyl, no more than three of $R_2$, $R_3$, $R_4$ and $R_5$ are hydrogen; $R_2$ is hydrogen, an alkyl radical containing 1 to 8 carbon atoms, and methoxy or phenyl when $R_3$, $R_4$ and $R_5$ are hydrogen, or when $R_3$ and $R_4$ are hydrogen and $R_5$ is methyl; $R_3$ is methyl when $R_4$ is methyl or hydrogen and $R_2$ and $R_5$ are hydrogen; $R_4$ is hydrogen, an alkyl radical containing 1 to 8 carbon atoms, a cycloalkyl radical containing 3 to 6 carbon atoms, a t-alkyl radical containing 4 to 8 carbon atoms, methoxy, phenyl, halogen or methoxycarbonyl, when $R_2$ is hydrogen, an alkyl radical containing 1 to 8 carbon atoms, a cycloalkyl radical containing 3 to 6 carbon atoms and a t-alkyl radical containing 4 to 8 carbon atoms, and $R_3$ and $R_5$ are hydrogen; $R_5$ is methyl when $R_2$, $R_3$ and $R_4$ are hydrogen, or when $R_4$ is methyl and $R_2$ and $R_3$ are hydrogen, and hydrogen when $R_2$, $R_3$, $R_4$ are the same as above; and when $R_4$ and $R_5$ are (—CH=$CR_7$—CH=CH—), $R_7$ is hydrogen or t-butyl, and $R_2$ is t-butyl or hydrogen and $R_3$ is hydrogen; and when $R_2$ and $R_3$ are (—CH=CH—)$_2$, R$_4$ and R$_5$ are hydrogen; and at least one of said R$_2$, R$_3$, R$_4$ and R$_5$ is an alkyl radical containing 1 to 8 carbon atoms; and (2) hydroxyphenylalkyleneyl isocyanurates of the formula

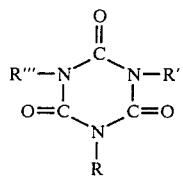

wherein R' is a hydroxyphenylalkyleneyl radical of the formula

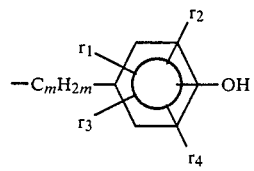

where m is 1 to 4, r$_1$ is an alkyl radical having 1 to 18 carbon atoms and is positioned immediately adjacent to the hydroxy group on the ring; r$_2$, r$_3$ and r$_4$ are hydrogen or an alkyl radical containing 1 to 18 carbon atoms; and R'' and R''' are hydrogen, an alkyl radical containing 1 to 18 carbon atoms, or are the same as r'; and R'' and R''' are hydrogen, an alkyl radical containing 1 to 18 carbon atoms, or are the same as R'.

12. A composition of claim 11 wherein in (1) R$_1$ is hydrogen, a primary, secondary or tertiary alkyl group containing 1 to 4 carbon atoms, or a —CH$_2$CH$_2$COOR$_6$ group wherein R$_6$ is an alkyl radical containing 1 to 4 carbon atoms; R$_2$ is hydrogen, a primary, secondary or tertiary alkyl group containing 1 to 4 carbon atoms; R$_3$ is hydrogen or methyl; R$_4$ is hydrogen or a primary, secondary or tertiary alkyl radical containing 1 to 4 carbon atoms; and R$_5$ is hydrogen.

13. A composition of claim 12 wherein in (2) R'' and R''' are equal to R', r$_1$ is a tertiary alkyl radical containing 4 to about 12 carbon atoms, r$_2$ is an alkyl radical containing 1 to about 12 carbon atoms, r$_3$ and r$_4$ are hydrogen, and m=1.

14. A composition of claim 13 where (2) has the formula

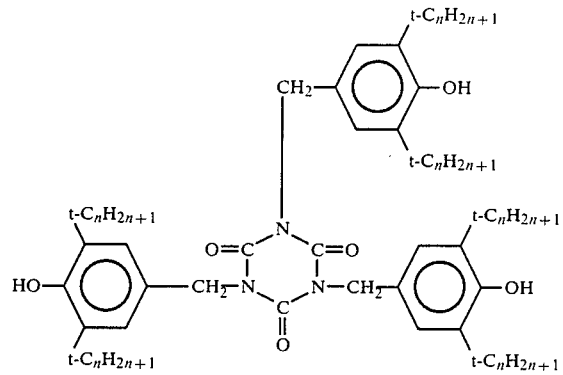

where n is 4 to 8.

15. A composition of claim 14 where (2) is 1,35,-tris(3,5-di-t-butyl-4-hydroxybenzyl)isocyanurate.

16. A composition of claim 15 wherein said polyolefin is polypropylene and (1) is 2-[4-methyl-2,6-bis(1,1-dimethylethyl)phenoxy]-6-methyl-4H-1,3,2-benzodioxaphosphorin.

17. A composition of claim 15 wherein said polyolefin is polypropylene and (1) is 2-[4-methyl-2,6-bis(1,1-dimethylethyl)phenoxy]-6,8-dimethyl-4H-1,3,2-benzodioxaphosphorin.

18. A composition of claim 15 wherein said polyolefin is polypropylene and (1) is 2-[2,4,6-tris(1,1-dimethylethyl)phenoxy]-6,8-dimethyl-4H-1,3,2-benzodioxaphosphorin.

* * * * *